US006224605B1

(12) United States Patent
Anderson et al.

(10) Patent No.: US 6,224,605 B1
(45) Date of Patent: May 1, 2001

(54) ORTHOPAEDIC INSTRUMENTATION ASSEMBLY AND METHOD OF USING SAME

(75) Inventors: Michael Anderson, Milwaukee, WI (US); Rodney Bays, Pierceton, IN (US); John Cooper, Sydney (AU); Lisa Schroder, Rochester, IN (US)

(73) Assignee: Bristol-Myers Squibb Co., New York, NY (US)

( * ) Notice: Subject to any disclaimer, the term of this patent is extended or adjusted under 35 U.S.C. 154(b) by 0 days.

(21) Appl. No.: 09/448,786

(22) Filed: Nov. 24, 1999

(51) Int. Cl.$^7$ .................................................. A61B 17/00
(52) U.S. Cl. ............................................................ 606/85
(58) Field of Search ................................... 606/1, 53, 79, 606/85, 86, 96, 98, 102, 116, 89; 623/923

(56) References Cited

U.S. PATENT DOCUMENTS

| | | |
|---|---|---|
| 4,959,066 | 9/1990 | Dunn et al. . |
| 5,169,401 | * 12/1992 | Lester et al. ............................ 606/79 |
| 5,342,362 | * 8/1994 | Kenyon et al. ......................... 606/79 |
| 5,578,037 | 11/1996 | Sanders et al. . |
| 5,607,431 | * 3/1997 | Dudasik et al. ........................ 606/86 |
| 5,683,395 | * 11/1997 | Mikhail .................................. 606/86 |
| 5,792,143 | * 8/1998 | Samuelson et al. ................... 606/102 |

OTHER PUBLICATIONS

Dunn, Anatomic Hip Prosthesis: Surgical Technique for Primary Hip Arthroplasty, 1989, pp. 1–19, University of Utah School of Medicine, Salt Lake City, Utah.

Gustilo and Kyle, Bias Total Hip System Surgical Technique, 1989, pp. 19–36, Hennepin County Medical Center, Minnesota.

Echelon Revision System, Aug. 1998, pp. 7, 8, 10, Smith+Nephew, Inc., Memphis, TN.

Ultima Calcar Stem, 1997, HOT–204, Johnson & Johnson Orthopaedics, USA.

Berman, hnr–pc, Head/Neck Replacement System Surgical Technique, Jun. 1993,6240–0–024 10M, Howmedica Inc., Rutherford, NJ.

Endurance Total Hip System, 1994, 10M1294 0611–03–000 (Rev.1), DePuy Inc., Warsaw, IN.

Meridian Definition Femoral Components: Command Instruments: Product Information & Technique Highlights, 1995, 6262–0–012–0 1M. Howmedica. Inc. Rutherford. NJ.

Osteonics, Surgical Protocol, The OMNIFIT Specialty Femoral System, p. 10, 1992, Lit. No. LSP–29, Osteonics Corp., Allendale, NJ.

* cited by examiner

*Primary Examiner*—Jeffrey A. Smith
*Assistant Examiner*—Eduando C. Robert
(74) *Attorney, Agent, or Firm*—Cary R. Reeves

(57) ABSTRACT

An orthopaedic instrumentation assembly for preparing a bone to receive an orthopaedic implant includes a rasp which is insertable within an opening in the bone and has an attachment end with a projection extending therefrom. A handle is attached to the projection. A cutting guide has a first leg and an adjoining second leg. The first leg is attached to the rasp and/or handle adjacent to the attachment end. The second leg is disposed at an obtuse angle relative to the first leg to thereby lie adjacent to the bone. The second leg includes at least one visual indicia thereon for marking the bone

16 Claims, 5 Drawing Sheets

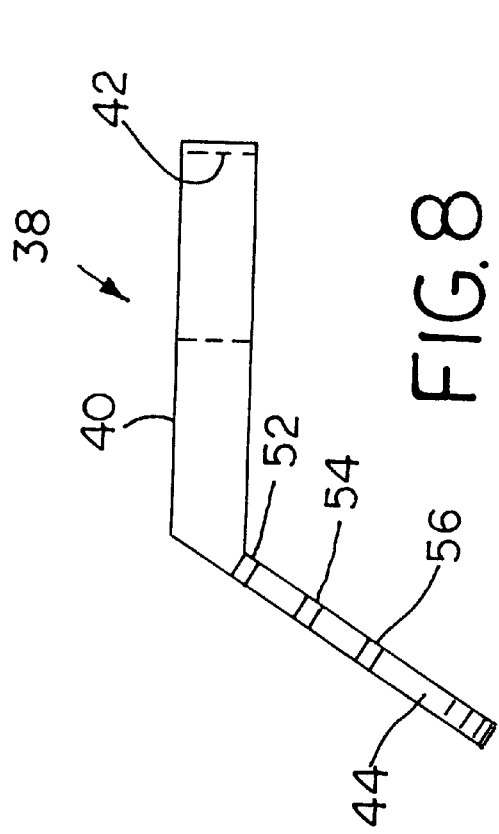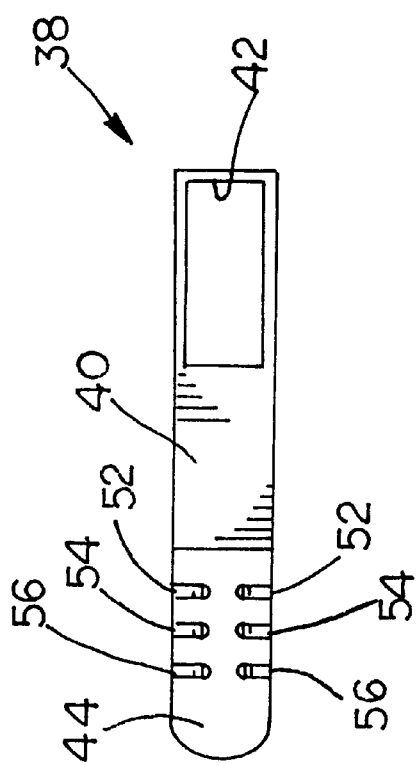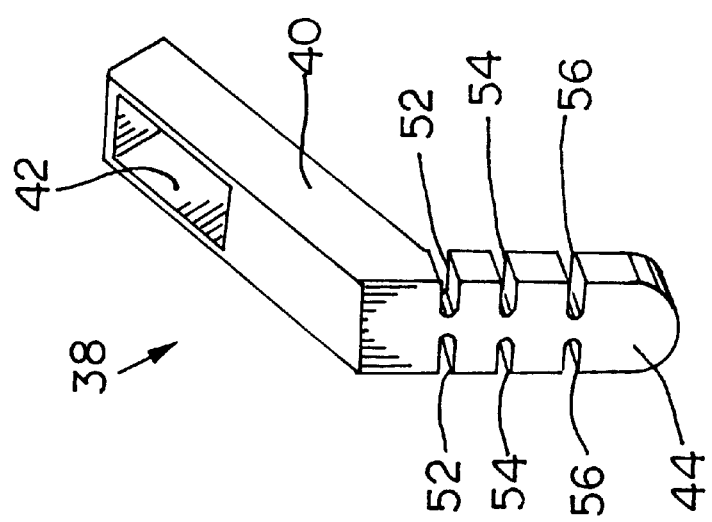

ORTHOPAEDIC INSTRUMENTATION ASSEMBLY AND METHOD OF USING SAME

BACKGROUND OF THE INVENTION

1. Field of the Invention

The present invention relates to an orthopaedic instrumentation assembly, and, more particularly, to an orthopaedic instrumentation assembly used to prepare a proximal femur for a calcar replacement stem.

2. Description of the Related Art

In orthopaedic hip surgery, the femoral head and neck bone is removed and a femoral stem implant is inserted into the proximal femur. In the process of removing the proximal bone, an osteotomy guide is typically used to mark the location for making the bone cuts. U.S. Pat. No. 4,959,066 teaches such an osteotomy guide. A cylindrical reamer is used to ream along the intramedullary canal of the femur and establish an axial reference. The osteotomy guide is attached to the reamer such that the guide lies along the outside of the femur. Indicia on the osteotomy guide are used to locate the guide relative to landmarks on the femur such as the femoral head center, greater trochanter and lesser trochanter. A slot in the guide is then used to mark the location of the bone cut corresponding to a desired implant position. The guide is removed and the femoral bone is cut and removed. Once the head and neck bone are removed, the intramedullary canal is rasped to seat the implant at the desired position. A calcar planer is often attached to the final rasp and rotated back and forth to precisely trim the bone cut made during the osteotomy step.

During an orthopaedic revision surgery, a primary orthopaedic implant which was placed within the bone during a previous primary surgery is removed and a revision orthopaedic implant is implanted within the bone. In the case of a revision surgery on a proximal femur, a femoral orthopaedic implant is removed from the bone and a revision femoral implant is placed within the proximal femur. When the primary femoral implant is removed, the proximal femur is prepared to receive the revision implant. It is often times desirable or necessary to remove a portion of the bone which was lying immediately adjacent to the primary implant. Additionally, it is usually necessary to further prepare and shape the intramedullary canal in which the implant is disposed. Depending upon the condition of the bone, more or less bone may be removed to receive the revision implant. It is desirable to leave as much bone as possible, while still ensuring that the revision implant seats against good bone with properly shaped complimentary mating surfaces.

If an appreciable amount of calcar bone must be removed from the proximal end of the femur during a revision surgery, it is known to use a calcar replacement stem which is specially configured to occupy the removed portion of the calcar such that the calcar replacement stem and proximal femur properly conform to and mate with each other. More particularly, a calcar replacement stem includes a block with a distal ledge extending generally transverse to the anatomical axis of the intramedullary canal in which the calcar replacement stem is disposed. Depending upon the amount of calcar bone removed, the surgeon may select a calcar replacement stem with a distal ledge which is disposed at a corresponding axial distance from the proximal end of the femur (i.e., at a selected location along the anatomical axis of the proximal femur).

To prepare a proximal femur for a calcar replacement stem as described above, a surgeon typically approximates the amount of bone to be cut or measures the bone with calipers. This process may be relatively time consuming and may require that the proximal femur be re-cut to properly mate with the calcar replacement stem. A typical prior art surgical technique for a calcar stem is shown in the Echelon Revision System brochure, published by Smith+Nephew. In this technique an osteotomy guide, similar to those used in primary surgeries, is held adjacent the femur and indicia are used to position it relative to the greater trochanter. Horizontal slots in the guide correspond to the calcar stems and the slots are used to mark the bone for cutting. After the bone is cut to the desired level, a cylindrical reamer is used to ream the intramedullary canal. A mark on the reamer is aligned with the bone cut to establish the reaming depth. After reaming, a series of broaches are impacted into the canal to broach the canal to the shape of the implant. A line on the broach is aligned with the bone cut to establish the broaching depth relative to the bone cut.

One shortcoming of the prior techniques is the reliance on landmarks which in a revision case may be significantly deteriorated or missing entirely. Another shortcoming is that the bone resection level is first determined and then the rasps, and ultimately the implant, are referenced to this predetermined level. In a revision case, the bone is deficient and implant stability may not be obtainable at a predetermined resection level.

What is needed in the art is an orthopaedic instrumentation assembly and method of using the same which provides fast and accurate locating, measuring and cutting of a proximal femur for receiving a calcar replacement stem. Further, what is needed is instrumentation and a technique that ensures both that the implant is stable and that the calcar stem seats on the bone.

SUMMARY OF THE INVENTION

The present invention provides an orthopaedic instrumentation assembly for a proximal femur including a cutting guide which is attached to a handle and/or rasp and has a plurality of visual indicia such as notches for marking and cutting the bone to receive a calcar replacement stem.

The invention comprises, in one form thereof, an orthopaedic instrumentation assembly for preparing a bone to receive an orthopaedic implant. A rasp insertable within an opening in the bone includes an attachment end with a projection extending therefrom. A handle is attached to the projection. A cutting guide has a first leg and an adjoining second leg. The first leg is attached to the rasp and/or handle adjacent to the attachment end. The second leg is disposed at an obtuse angle relative to the first leg to thereby lie adjacent to the bone. The second leg includes at least one visual indicia thereon for marking the bone.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 7 is a perspective view of the cutting guide shown in FIG. 3;

FIG. 8 is a side view of the cutting guide shown in FIG. 3; and

FIG. 9 is a top view of the cutting guide shown in FIG. 3.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
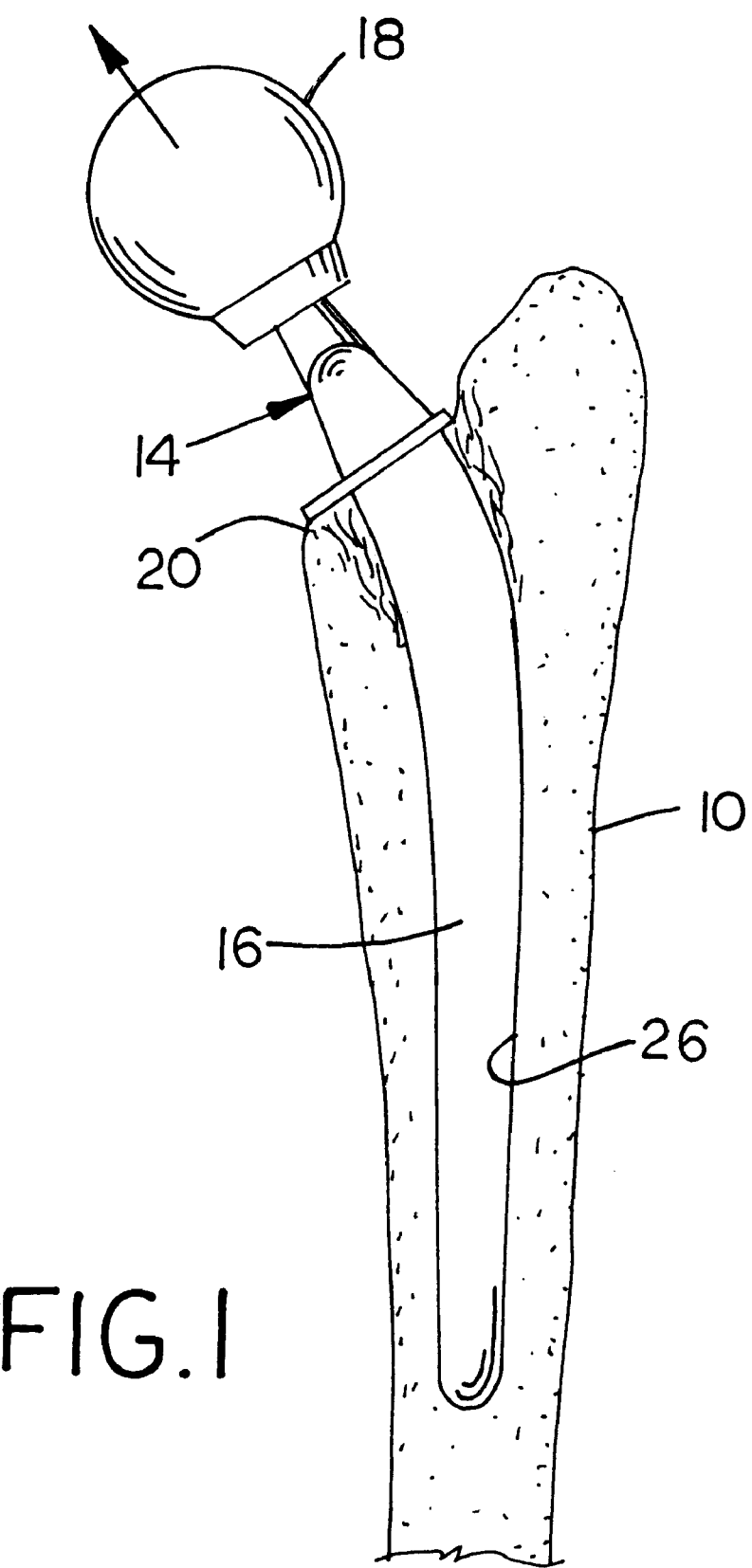
FIG. 1 is a side, partial-sectional view of a primary implant disposed within a proximal femur.
Figures 2, 3:
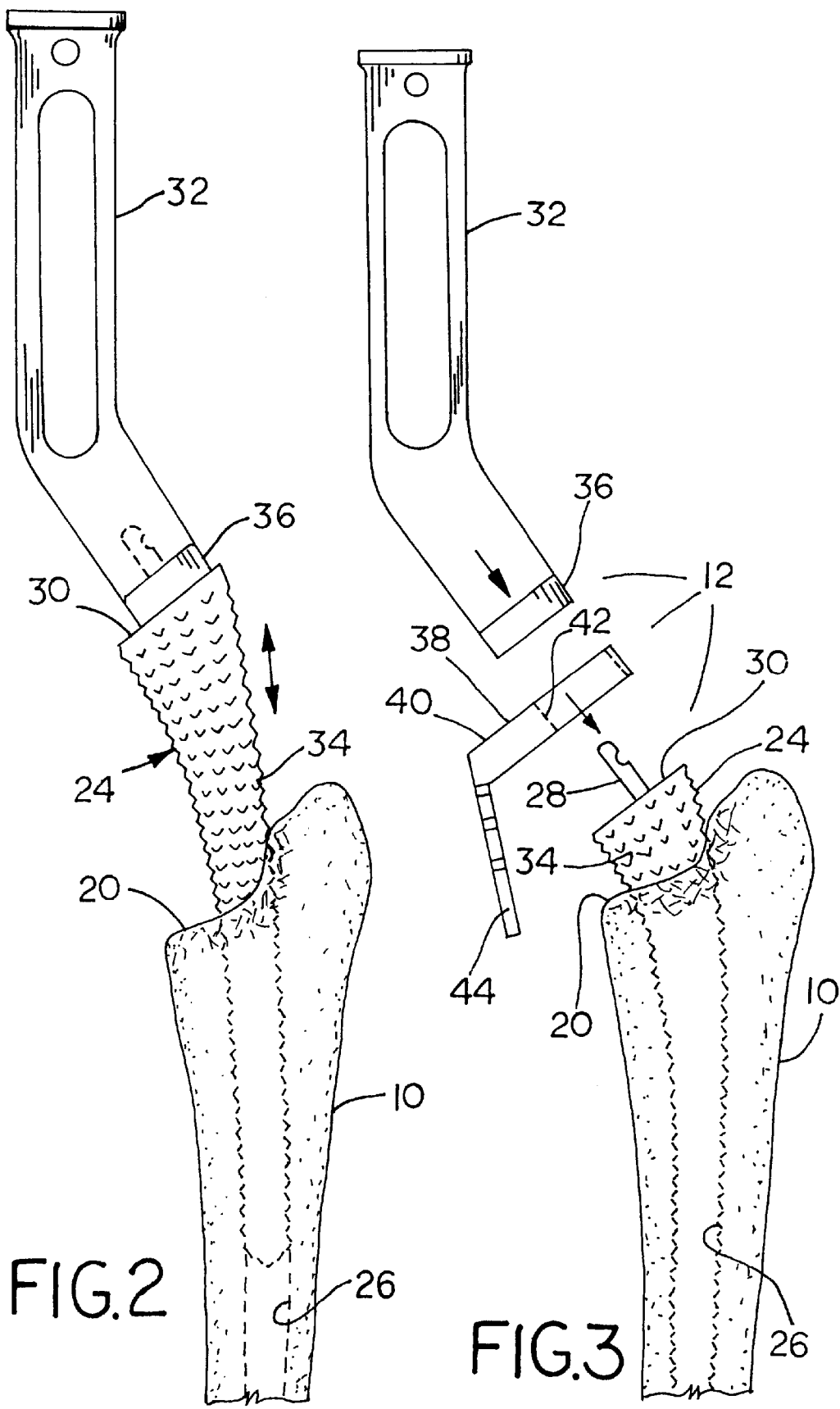
FIG. 2 is side view of a rasp being inserted or removed from the proximal femur according to the present invention.
FIG. 3 is a side view illustrating the rasp of FIG. 2 within the intramedullary canal of the proximal femur and a cutting guide and handle according to the present invention.

Referring now to the drawings, a method of preparing a proximal femur 10 using an embodiment of an orthopaedic instrumentation assembly 12 (FIG. 4) of the present invention during a revision surgery will be described.

FIG. 1 illustrates a proximal femur 10 with a primary implant 14 disposed therein which was previously implanted during a primary orthopaedic surgery. Primary implant 14 includes a stem 16 and a head 18, in known manner. Primary implant 14 may be removed from proximal end 20 of femur 10 using appropriate instrumentation (not shown). An enlarged opening within intramedullary canal 26 generally corresponding to the shape and size of stem 16 remains within proximal end 20 of femur 10 when primary implant 14 is removed therefrom.

Figure 6:
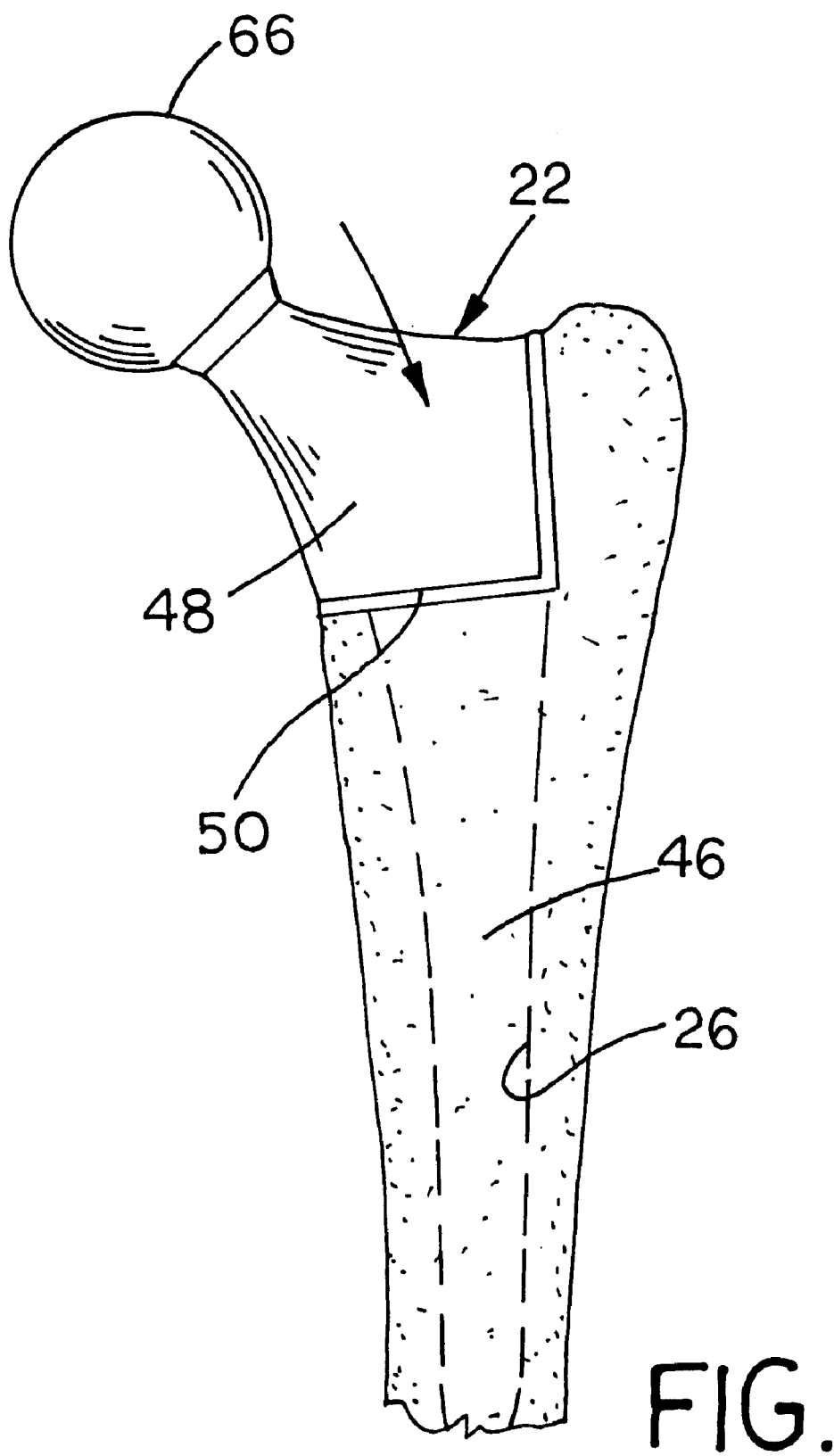
FIG. 6 is a side view with a revision implant having a calcar replacement stem inserted within the proximal femur.

After primary implant 14 is removed from femur 10, proximal end 20 must be properly prepared for receiving a revision implant 22 (FIG. 6). Accordingly, a plurality of sequentially larger rasps with an outside shape corresponding generally to the shape of revision implant 22 are placed within and impacted into intramedullary canal 26 within femur 10 (one of which is shown and referenced 24 in FIG. 4). Each rasp 24 includes a projection in the form of a trunnion 28 which extends generally orthogonal from an attachment end 30 thereof. Trunnion 28 allows rasp 24 to be removably attached with a handle 32. Handle 32 is oriented relative to stem 34 of rasp 24 such that movement of handle 32 in a generally longitudinal direction by a surgeon in turn causes stem 34 to move in a direction generally parallel with a longitudinal axis of intramedullary canal 26. Handle 32 also includes an opposite end which may be impacted with a hammer or the like for impacting rasp 24 within intramedullary canal 26. Thus, axial movement of handle 32 in turn causes axial movement of stem 34 without exerting undue torque loads on femur 10. Sequential rasping is continued until the desired, stable, bone-to-rasp fit is achieved. Each rasp corresponds to a particular size and shaped implant stem. Thus, when the final rasp is seated in a stable position, it is located where the corresponding implant will rest when it is implanted.

Figure 4:
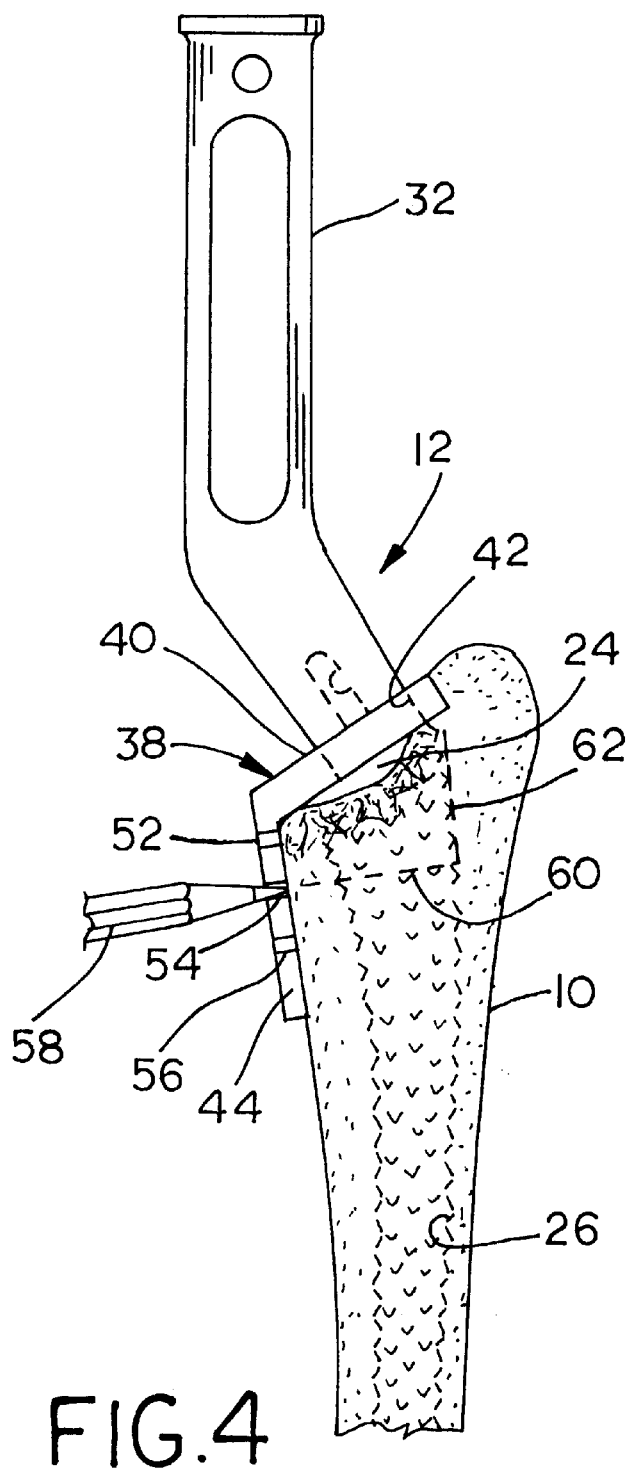
FIG. 4 is a side view illustrating the use of the rasp, cutting guide, and handle of FIG. 3.

After intramedullary canal 26 is rasped to a desired size using sequentially larger rasps 24, handle 32 is removed from attachment end 30 of rasp 24. Handle 32 includes an abutment block 36 which abuts against attachment end 30 of rasp 24. A cutting guide 38 includes a first leg 40 with an opening 42 formed therein. Opening 42 has a cross-sectional shape and size which is configured to slide over and matingly conform in a relatively tight manner with abutment block 36 of handle 32. Handle 32 is then reattached with trunnion 28 such that handle 32, cutting guide 38 and rasp 24 are attached to each other in substantially an immovable manner (FIG. 4).

Cutting guide 38 also includes a second leg 44 which is attached to and disposed at an obtuse angle relative to first leg 40. In the embodiment shown, second leg 44 is disposed at an angel of approximately 120° relative to first leg 40. The obtuse angle between second leg 44 and first leg 40 is selected such that second leg 44 lies substantially adjacent to femur 10 (FIG. 4). Second leg 44 also includes at least one visual indicia thereon which allows femur 10 to be marked for cutting using a suitable marking instrument, such as a marking pencil 58. Revision implant 22 includes a calcar replacement stem 46 with a calcar block 48 having a distal ledge 50. Distal ledge 50 may be positioned, on alternative blocks 48, at one of a plurality of distances from proximal end 20, dependent upon the extent of the bone to be removed. If a larger amount of the calcar portion of femur 10 is to be removed, then distal ledge 50 is disposed further away from proximal end 20; and if a smaller amount of the calcar portion is to be removed, distal ledge 50 is closer to proximal end 20. The visual indicia in the form of notches 52, 54 and 56 correspond to the placement location of distal ledge 50, dependent upon the amount of bone to be removed. In the embodiment shown, notch 56 is used to mark the calcar portion of femur 10 for subsequent cutting using a suitable marking instrument such as a marking pencil 58, as indicated by dash line 60. A second cut 62 extending generally parallel to an anatomical axis of intramedullary canal 26 is made by the surgeon in a direction generally orthogonal to line 60. The ledge 50, should fit closely with the calcar bone and at the same time the stem should be stable within the intramedullary canal. With the cutting guide 38 referenced to the well seated rasp, which in turn corresponds to the implant, the use of this instrument and technique results in a bone resection wherein the calcar is well fitting and the stem is stable.

Figure 5:
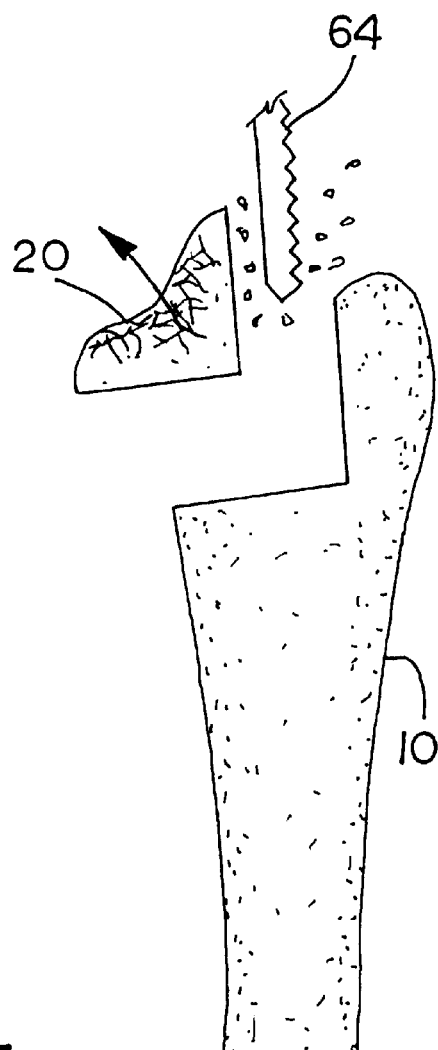
FIG. 5 is a side view of the proximal femur illustrating a part of the calcar portion being cut away.

After femur 10 is marked using cutting guide 38, rasp 24 is removed from within intramedullary canal 26 (FIG. 5), and a suitable saw 64 or other cutting instrument is used to cut femur 10 along lines 60 and 62. Thus, a predetermined amount of the calcar portion is removed from femur 10 (FIG. 5).

Revision implant 22 is then implanted within femur 10 such that stem 46 is received within the prepared intramedullary canal 26 and distal ledge 50 abut against femur 10. Head 66 of revision implant 22 engages against an acetabular cup within a prepared acetabulum in known manner.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic instrumentation assembly for preparing a bone to receive an orthopaedic implant stem, said orthopaedic assembly comprising:

a rasp for insertion into an opening in the bone, said rasp corresponding in size and shape to said orthopaedic implant stem and having an attachment end with a projection extending therefrom;

a handle attached to said projection; and a cutting guide having a first leg and an adjoining second leg, said first leg attached to at least one of said rasp and said handle, said second leg disposed at an obtuse angle relative to said first leg to thereby be configured to lie adjacent to the bone, said second leg including at least one visual indicia thereon for marking the bone.

2. The orthopaedic assembly of claim 1, wherein said first leg of said cutting guide includes an opening, and wherein said handle includes an abutment block which abuts against said attachment end of said rasp and is disposed within said opening.

3. The orthopaedic assembly of claim 2, wherein said opening is generally rectangular shaped in cross section.

4. The orthopaedic assembly of claim 2, wherein said opening is configured to prevent relative movement between said cutting guide and said handle.

5. The orthopaedic assembly of claim 1, wherein said at least one visual indicia comprises a plurality of notches.

6. The orthopaedic assembly of claim 5, wherein said second leg includes opposing side edges, and said plurality of notches are disposed in each of said side edges.

7. The orthopaedic assembly of claim 6, wherein three of said notches are disposed in each of said side edges.

8. The orthopaedic assembly of claim 1, wherein said rasp has a longitudinal axis and wherein said second leg is aligned with said longitudinal axis.

9. The orthopaedic assembly of claim 1, wherein said rasp comprises a proximal femoral rasp.

10. A method of preparing a proximal femur during a revision surgery to receive a calcar replacement stem, comprising the steps of:

removing a primary orthopaedic implant from an intramedullary canal within the proximal femur;

providing a rasp corresponding in size and shape to said calcar replacement stem;

attaching a handle to an attachment end of said rasp;

rasping the intramedullary canal using said rasp;

seating said rasp in the canal at the desired location of said calcar replacement stem;

attaching a first leg of a cutting guide to at least one of said handle and said rasp adjacent said attachment end of said rasp, said cutting guide having a second leg adjoining said first leg, said second leg disposed at an obtuse angle relative to said first leg and having at least one visual indicia;

locating said second leg of said cutting guide adjacent a calcar portion of said bone;

marking said calcar portion of said bone using said at least one visual indicia; and cutting said calcar portion of said bone at said mark.

11. The method of claim 10, comprising the further step of removing said cut calcar portion of said bone.

12. The method of claim 10, wherein said handle includes an abutment block which abuts against said attachment end of said rasp, and wherein said first leg of said cutting guide includes an opening with a shape corresponding to said abutment block, said attaching step comprising placing said abutment block within said opening.

13. The method of claim 12, wherein said opening is generally rectangular shaped in cross section.

14. The method of claim 10, wherein said calcar replacement stem has a calcar block with a distal ledge, and wherein at least one of said visual indicia corresponds to a seating location of said distal ledge after said femur is prepared.

15. The method of claim 10, wherein said at least one visual indicia comprises a plurality of notches.

16. The method of claim 15, wherein said second leg includes opposing side edges, and said plurality of notches are disposed in each of said side edges.

* * * * *